United States Patent [19]

Lin et al.

[11] Patent Number: 4,710,492

[45] Date of Patent: Dec. 1, 1987

[54] 3'-AZIDO-2',3'-DIDEOXY-5-HALOURIDINE AND ITS USE IN TREATING PATIENTS INFECTED WITH RETROVIRUSES

[75] Inventors: Tai-Shun Lin, North Haven; William H. Prusoff, North Branford, both of Conn.

[73] Assignee: Yale University, New Haven, Conn.

[21] Appl. No.: 677,656

[22] Filed: Jun. 23, 1986

[51] Int. Cl.$^4$ .................. A61K 31/70; C07H 17/00
[52] U.S. Cl. ............................ 514/50; 536/23; 514/934
[58] Field of Search ............... 514/49, 50, 934; 536/23

[56] References Cited

U.S. PATENT DOCUMENTS 4,604,382  8/1986  Lin et al. ........................... 514/49

OTHER PUBLICATIONS

*Journal of Medicinal Chemistry*, 21, 109, (1978), "Synthesis and Biological Activity of Several Amino Analogues of Thymidine", by Tai-Shun Lin and William H. Prusoff.
*Journal of Medicinal Chemistry*, 21, 106, (1978), "A Novel Synthesis and Biological Activity of Several 5-Halo-5'-Amino Analogues of Deoxyribopyrimidine Nucleosides", by Tai-Shun Lin and William H. Prusoff.
*Journal of Medicinal Chemistry*, 26, 1691 (1983), "Synthesis and Biological Activity of Various 3'-Azido and 3'-Amino Analogues of 5-Substituted Pyrimidine Deoxyribonucleosides", by Tai-Shin Lin, You-Song Gao & William R. Mancini.
*Proc. Natl. Acad. Sci. USA*, 82, 7096, (1985), "3'-Azido-3'-3'-Deoxythymidine (BW A509U): An Antiviral Agent that Inhibits the Infectivity and Cytopathic Effect of Human T-Lymphotropic Virus Type III/Lymphadenopathy-Associated Virus *In Vitro*", by Hiroaki Mitsuya, Kent J. Weinhold, Phillip A. Furman, Marty H. St. Clair, Sandra Nusinoff Lehrman, Robert C. Gallo, Dani Bolognesi, David W. Barry and Samuel Broder.

*Primary Examiner*—J. R. Brown
*Assistant Examiner*—John W. Rollins, Jr.
*Attorney, Agent, or Firm*—Sprung Horn Kramer & Woods

[57]  ABSTRACT

This invention relates to 3'-azido-2',3'-dideoxy-5-halouridine, particularly, 3'-azido-2', 3'-dideoxy-5-bromouridine and 3'-azido-2',3'-dideoxy-5-iodouridine, and its use in treating patients infected with a retrovirus.

19 Claims, No Drawings

3'-AZIDO-2',3'-DIDEOXY-5-HALOURIDINE AND ITS USE IN TREATING PATIENTS INFECTED WITH RETROVIRUSES

GOVERNMENT RIGHTS

This invention was made with United States government support under Grant CA-28852 from the NIH. The United States Government has certain rights in this invention.

BACKGROUND OF THE INVENTION

1. Field of the Invention

The present invention concerns a new nucleoside having anti-retrovirus activity. More particularly, the present invention concerns 3'-azido-2',3'-dideoxy-5-halouridine.

2. Background Information

Applicants Tai-Shun Lin and William H. Prusoff heretofore explored the biological potential of the 3'- and the 5'-amino analogues of thymidine ("Synthesis and Biological Activity of Several Amino Analogues of Thymidine", Journal of Medicinal Chemistry, 21, 109, (1978)), wherein 3',5'-diamino-3',5'-dideoxythymidine, 3'-amino-3'-deoxythymidine, 5'-amino-5'-deoxythymidine, 3'-azido-5'-O-p-tolylsulfonyl-3'-deoxythymidine and 3',5'-diazido-3',5'-dideoxythymidine were prepared and evaluated.

In "A Novel Synthesis and Biological Activity of Several 5-Halo-5'-Amino Analogues of Deoxyribopyrimidine Nucleosides", Journal of Medicinal Chemistry, 21, 106, (1978), applicants Tai-Shun Lin and William H. Prusoff reported a synthetic prodedure for the synthesis of 5-chloro, 5-bromo and 5-iodo-5'-amino-2',5'-dideoxyuridine, as well as two analogues, 5-iodo-5'-amino-2',5'-dideoxycytidine and 5-fluoro-5'-amino-2',5'-dideoxyuridine, in good yield.

In "Synthesis and Biological Activity of Various 3'-Azido and 3'-Amino Analogues of 5-Substituted Pyrimidine Deoxyribonucleosides", Journal of Medicinal Chemistry, 26, 1691, (1983) by Tai-Shun Lin, You-Song Gao and William R. Mancini, the following compounds were synthesized and evaluated: 3'-amino-2',3'-dideoxy-5-fluorouridine; 3'-amino-2',3'-dideoxycytidine and 3'-amino-2',3'-dideoxy-5-fluorocytidine.

Hiroaki Mitsuya, Kent J. Weinhold, Phillip A. Furman, Marty H. St. Clair, Sandra Nusinoff Lehrmann, Robert C. Gallo, Dani Bolognesi, David W. Barry and Samuel Broder, "3'-Azido-3'-Deoxythymidine (BW A 509 U): An Antiviral Agent that Inhibits the Infectivity and Cytopathic Effect of Human T-Lymphotropic Virus Type III/Lymphadenopathy—Associated Virus In Vitro", Proc. Natl. Acad. Sci. USA, 82, 7096, (1985) described the use of 3'-azido-3'-deoxythymidine to inhibit HTLV III/LAV replication and to block the cytopathic effects of HTLV III/LAV in vitro.

SUMMARY OF THE INVENTION

There has been discovered a new class of nucleosides, namely, 3'-azido-2',3'-dideoxy-5-halouridines which have anti-retrovirus activity.

The present invention is directed to the treatment of warm blooded animals, including humans, infected with a retrovirus comprising administering to a warmblood animal, e.g., a human patient an anti-retroviral effective amount of 3'-azido-2',3'-dideoxy-5-halouridine, either alone or in admixture with a diluent or in the form of a medicament.

DETAILED DESCRIPTION OF THE INVENTION

The structure of 3'-azido-2',3'-dideoxy-5-halouridine ($C_9H_{10}N_5O_4R$) according to the present invention is as follows:

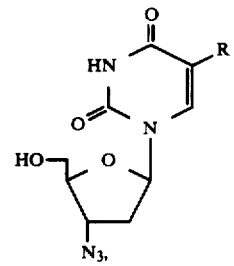

wherein R is Br, I or Cl, preferably Br.

3'-azido-2',3'-dideoxy-5-halouridine has antiviral activity against retroviruses, e.g., murine leukemia virus and HTLV III/LAV virus (the AIDS virus).

Retroviruses are RNA viruses whose genome contains copies of high-molecular weight single-stranded RNA. The virion contains reverse transcriptase. Non-limiting examples of retroviruses include leukemia and sarcoma viruses of animals, foamy viruses of primates and some slow viruses, e.g., visna and maedi of sheep.

The synthesis of a compound according to the present invention is illustrated in the following reaction scheme:

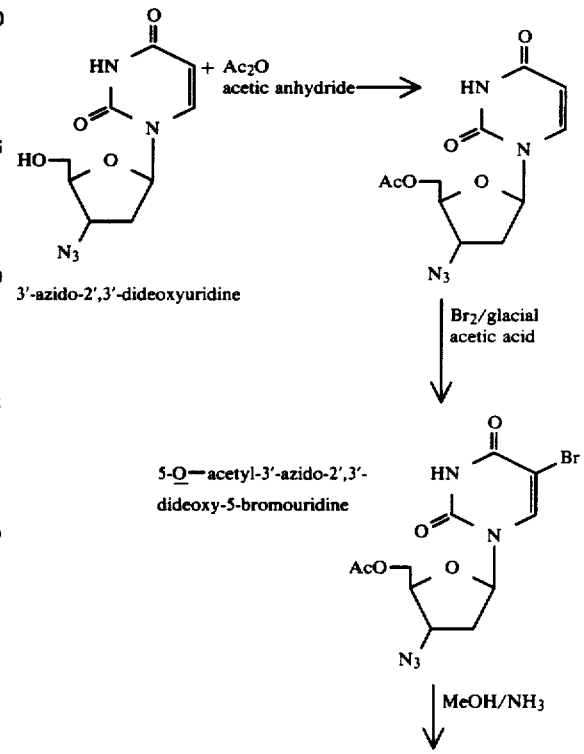

3'-azido-2',3'-dideoxyuridine

5-O—acetyl-3'-azido-2',3'-dideoxy-5-bromouridine

-continued

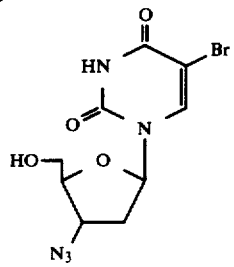

3'-azido-2',3'-dideoxy-5-bromouridine

As stated above, the invention also relates to the use in medicine of the compound of the invention.

The present invention provides a pharmaceutical composition containing as an active ingredient the compound of the invention in admixture with a solid, liquid or liquefied gaseous diluent.

The invention further provides a pharmaceutical composition containing as an active ingredient a compound of the invention in the form of a sterile and/or physiologically isotonic aqueous solution.

The invention also provides a medicament in dosage unit form comprising the compound of the invention.

The invention also provides a medicament in the form of tablets (including lozenges and granules), dragees, capsules, pills, ampoules or suppositories comprising the compound of the invention.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the compound of the invention in association with a carrier and/or enclosed within an envelope. Whether the medicament contains a daily dose, or for example, a half, a third or a quarter of a daily dose will depend on whether the medicament is to be administered once or, for example, twice, three times or four times a day, respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g., granulates) adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agaragar, calcium carbonate and sodium bicarbonate; (e) agents for retarding dissolution, e.g., paraffin; (f) resorption accelerators, e.g, quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together, with one or several of the above mentioned diluents.

The diluents to be used in pharmaceutical compositions adapted to be formed into suppositories can, for example, be the usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and emulsions should be sterile and, if appropriate, blood-isotonic.

The pharmaceutical compositions which are suspensions can contain the usual diluents, such as liquid diluents, e.g., water, ethyl alcohol, propylene glycol, surface-active agents (e.g., ethoxylated isostearyl alcohols, polyoxyethylene sorbite and sorbitane esters) microcrystalline cellulose, aluminium metahydroxide, bentonite, agar-agar and tragacanth or mixtures thereof.

All the pharmaceutical compositions according to the invention can also contain color agents and preservatives, as well as perfumes and flavoring additions (e.g., peppermint oil and eucalyptus oil) and sweetening agents (e.g., saccharin and aspartame).

The pharmaceutical compositions according to the invention generally contain from 0.5 to 90% of the active ingredient by weight of the total composition.

In addition to the compound of the invention, the pharmaceutical compositions and medicaments according to the invention can also contain other pharmaceutically active compounds.

Any diluent in the medicaments of the present invention may be of those mentioned above in relation to the pharmaceutical compositions of the present invention. Such medicaments may include solvents of molecular weight less than 200 as the sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, may include a protective envelope which renders the portions of the medicament physically discrete and coherent.

The preferred daily dose for administration of the medicaments of the invention is 2.5 to 250 mg of active ingredient in the case of intravenous administration and 25 to 250 mg of active ingredient in the case of oral administration.

The product of the above-mentioned pharmaceutical compositions and medicaments is carried out be any method known in the art, for example, by mixing the active ingredient(s) with the diluents(s) to form a pharmaceutical composition (e.g., a granulate) and then forming the composition into the medicament (e.g. tablets).

This invention further provides a method for treating the above-mentioned diseases in warm-blooded animals, which comprises administering to the animals a compound of the invention alone or in admixture with a diluent or in the form of a medicament according to the invention.

It is envisaged that this active compound will be administered perorally, parenterally (for example, intramuscularly, intraperitoneally, subcutaneously or intravenously), rectally or locally, preferably orally or parenterally, especially perlingually or intravenously. Preferred pharmaceutical compositions and medicaments are, therefore, those adapted for administration such as oral or parenteral administration. Administration in the method of the invention is preferably oral or parenteral administration.

In general, it has proved advantageous to administer intravenously amounts of from 0.01 mg to 10 mg/kg, preferably 0.05 to 5 mg/kg, of body weight per day and to administer orally 0.05 to 20 mg/kg, preferably 0.5 mg to 5 mg/kg/ of body weight per day, to achieve effective results. Nevertheless, it can at times be necessary to deviate from those dosage rates, and in particular to do so as a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than the above-mentioned minimum dosage rate, whilst other cases the upper limit mentioned must be exceeded to achieve the desired results. Where larger amounts are administered, it may be advisable to divide these into several individual administrations over the course of the day.

The invention will now be described with reference to the following non-limiting examples.

EXAMPLE 1

Synthesis of 3'-azido-2'-3-'dideoxy-5-bromouridine (3'-N$_3$-BUdR, LTS-V-167)

A suspension of 3'-azido-2',3'-dideoxyuridine (1.0 g, 3.95 mmol) in 25 ml of acetic anhydride was heated until dissolution occurred (oil bath temperature of approximately 100° C. used). A solution of bromine (0.7 g, 4.35 mmol) in 3 ml of glacial acetic acid was added to the above solution with cooling, to maintain a temperature of 25° C. After being maintained overnight in the cold (4 C.), the solution was evaporated to dryness under reduced pressure (vacuum pump utilized) to yield 3'-azido-5'-O-acetyl-2',3'-dideoxy-5-bromouridine as a thick yellow syrup, which was disclosed immediately in 50 mL of absolute methanol containing 7 g of anhydrous ammonia. This solution was then kept at 4° C. for 48 hours. The solvent was removed in vacuo at 30° C. and then residue chromatographed on silica gel column (CH$_2$Cl$_2$:EtOAc, 1:1). The fractions containing the desired product (R$_f$=0.51) were pooled together and the solvent evaporated in vacuo to afford 0.55 g (42%) of white plate-like crystals mp 150–151° C.; IR (KBr) 4.70 (azido) μm; UV (EtOH)λmax 278 nm (ε14,300), UV (EtOH) λmin 240 nm, UV (0.1 N HCl)λmax 278 nm (ε9,400), UV (0.1 N HCl)λmin 240 nm, UV (0.1 N NaOH)λmax 274 nm (ε6,800), UV (0.1 N NaOH)λmin 248 nm; NMR (DMSO-d$_6$) ε2.28–2.33 (m, 1H, 2'-H$_a$) 2.42–2.46 (m, 1H, 2'-H$_b$), 3.59 (d, 1H, 5'-H$_a$), 3.68 (d, 1H, 5'-H$_b$), 3,83 (m, 1H, 4'-H), 4.37 (q, 1H, 3'-H), 5.35 (br s, 1H, 5'-OH, D$_2$O exchangeable), 6.01 (t, 1H, 1'-H), 8.37 (s, 1H, 6-H), 11.81 (br s, 1H, 3-NH, D$_2$O exchangeable).

Analysis Calculated for C$_9$H$_{10}$BrN$_5$O$_4$: C, 32.55; H, 3.04; Br, 24.06; N 21.09. Found: C, 32.60; H, 2.92; Br, 23.89; N, 21.36.

The key starting compound, 3'-azido-2',3'-dideoxyuridine (3'-N$_3$-UdR), was prepared via a multi-step synthesis from 2'-deoxyuridine by the procedure described in T. S. Lin and W. R. Mancini, *J. Med. Chem.*, 26, 544, (1983).

EXAMPLE 2

Biological Activity Assay Procedure for Antiviral Screening Against Moloney Murine Leukemia Virus (MuLV) by XC-Assay The XC assay system is an indirect method for quantitation of murine-leukemia virus (MuLV) originally described by V. Klement et al, *Proc. Natl. Acad. Sci.*, 63, 753, (1969) and modified by W. Rowe et al, *Virology*, 42, 1136, (1970). This test is based on the development of syncytial changes in the XC cell line when it is co-cultivated with mouse fibroblast cells (SC-1 cells) productively infected with MuLV. The XC cell line was derived from a rat tumor induced by the prague strain of Rouse Sarcoma Virus (RSV) (J. Svoboda et al, *Folia Biol.*, 9, 77, (1963)). This cell line contains the RSV genome, but does not produce infectious virus in the absence of a helper virus.

1E5 SC-1 cells were seeded, in Earls Minimum Essential Medium (EMEM)-10% Fetal Bovine Serum (FBS), onto 60 mm petri dishes. The following day, the cells were inoculated with 0.5 ml of a virus dilution containing 25 μg/ml of DEAE-dextran. The dishes were maintained for 1 hour at 37° C. in a humidified 5% CO$_2$ incubator. The virus inoculum was then removed and replaced with 5 ml of medium containing appropriate concentration of the test compound (two dishes/concentration). Medium containing 5% FBS was added to the virus control dishes. The medium (with or without the test compound) was changed at 48 hours.

Five days after virus inoculation, the culture fluid was decanted and the cells were irradiated with a GE germicidal bulb for 30 seconds (1500–1800 ergs UV-light). Cultures were immediately overlaid with 2E5 XC cells in 5 ml of EMEM-10% FBS/dish. The medium was changed at 2 day intervals. Four days after XC cell addition, cultures were simultaneously fixed and stained with GEIMSA for 10 to 15 minutes.

Plaques were counted using an inverted microscopy as holes in the cell sheet containing syncytial cells, or as focal masses of multinucleated giant cells.

Calculation of % Inhibition/Concentration:

% Inhibition/concentration =

-continued $$100 - \left[ \frac{\text{ave. \# of syncytia/conc of test comp.}}{\text{ave. \# of syncytia/in the virus control}} \times 100 \right]$$

ID50: Accumulative % Inhibition using Reed-Muench Method

The antiviral activity of 3'-azido-2',3'-dideoxy-5-bromouridine (3'-N₃-BUdR) and 3'-azido-2',3'-dideoxy-5-iodouridine (3'-N₃IUdR) compared against 3'-azido-3'-deoxythymidine were found to be as follows:

| Compound | ID50 (μM) (Moloney Murine Leukemia Virus) | ID50 μM HTLV-III/ LAV/AAV |
|---|---|---|
| 3'-N₃—BUdR | 1.5 | 2.3 |
| 3'-N₃—IUdR | 3.0 | |
| 3'-azido-3'-deoxy-thymidine | 0.023 | 0.23 |

It will be appreciated that the instant specification and claims are set forth by way of illustration and not limitation and that various modifications and changes may be made without departing from the spirit and scope of the present invention.

What is claimed is:

1. A 3'-azido-2',3'-dideoxy-5-halouridine compound having the formula

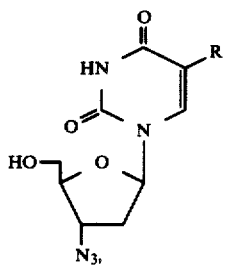

wherein R is a halogen selected from the group consisting of Br and Cl.

2. A 3'-azido-2',3'-dideoxy-5-halouridine according to claim 1, wherein R is Br.

3. A method for treating warm blooded animals infected with a retrovirus, the method comprising administering to the warm blooded animal an anti-retroviral effective amount of a 3'-azido-2',3'-dideoxy-5-halouridine compound having the formula

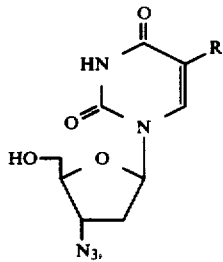

wherein R is a halogen selected from the group consisting of Br, Cl and I, either alone or in admixture with a diluent or in the form of a medicament.

4. A method according to claim 3, wherein the compound is 3'-azido-2',3'-dideoxy-5-bromouridine.

5. A method according to claim 3, wherein the compound is 3'-azido-2',3'-dideoxy-5-iodouridine.

6. A method according to claim 3, wherein the retrovirus is murine leukemia virus.

7. A method according to claim 3, wherein the retrovirus is HTLV III/LAV.

8. A method according to claim 3, wherein the 3'-azido-2',3'-dideoxy-5-halouridine is administered intravenously in an amount of 0.01 to 10 mg per kg body weight per day.

9. A pharmaceutical composition comprising as an active ingredient an anti-retroviral effective amount of a 3'-azido-2',3'-dideoxy-5-halouridine compound having the formula

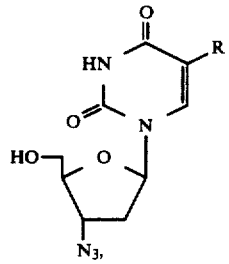

wherein R is a halogen selected from the group consisting of BR, Cl, and I, in admixture with a solid, liquid or liquefied gaseous diluent.

10. A pharmaceutical composition according to claim 9, wherein the compound is 3'-azido-2',3'-dideoxy-5-bromouridine.

11. A pharmaceutical composition according to claim 9, wherein the compound is 3'-azido-2',3'-dideoxy-5-ioduridine.

12. A pharmaceutical composition according to claim 9, containing 0.5 to 90% of said active ingredient.

13. A pharmaceutical composition according to claim 9 in the form of a sterile physiologically isotonic aqueous solution.

14. A pharmaceutical composition according to claim 9, containing 0.5 to 90% of said active solution ingredient.

15. A medicament in dosage unit form comprising an anti-retroviral effective amount of 3'-azido-2',3'-dideoxy-5-halouridine compound having the formula

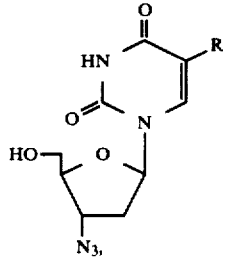

wherein R is a halogen selected from the group consisting of Br, Cl and I, and an inert pharmaceutical carrier.

16. A medicament according to claim 15, wherein the compound is 3'-azido-2',3'-dideoxy-5-bromouridine.

17. A medicament according to claim 15, wherein the compound is 3'-azido-2',3'-dideoxy-5-ioduridine.

18. A medicament according to claim 15, in the form of a tablet, pill, dragee, capsule, ampoule or suppository.

19. A 3'-azido-2',3'-dideoxy-5-halouridine according to claim 1, wherein R is Cl.

* * * * *

UNITED STATES PATENT AND TRADEMARK OFFICE
CERTIFICATE OF CORRECTION

PATENT NO. : 4,710,492

DATED : December 1, 1987

INVENTOR(S) : Tai-Shun Lin, et al.

It is certified that error appears in the above-identified patent and that said Letters Patent is hereby corrected as shown below:

| | |
|---|---|
| Title Page, No. "[21] Appl. No.:" | Delete "677,656" and substitute --877,656-- |
| Col. 1, line 67 | After "patient" insert --,-- |
| Col. 4, line 39 | Delete "color" and substitute --coloring-- |
| Col. 4, line 51 | After "be" insert --any-- |
| Col. 6, line 7 | Before "2.28" delete "$\varepsilon$" and substitute --$\delta$-- |
| Col. 8, line 41 | After "active" delete "solution" |
| Col. 8, line 63 | Correct spelling of --iodouridine-- |

Signed and Sealed this

Twenty-first Day of June, 1988

Attest:

DONALD J. QUIGG

*Attesting Officer*                *Commissioner of Patents and Trademarks*